United States Patent

Russell et al.

[11] Patent Number: 5,750,894
[45] Date of Patent: May 12, 1998

[54] MEASUREMENT OF TENSION USING NATURAL FREQUENCY OF VIBRATION

[75] Inventors: Jonathan C. Russell, South Glastonbury, Conn.; Thomas J. Lardner, Amherst, Mass.

[73] Assignee: The Government of the United States as represented by the Secretary of Transportation, Washington, D.C.

[21] Appl. No.: 778,024

[22] Filed: Oct. 31, 1996

[51] Int. Cl.$^6$ ................................................ G01N 29/12
[52] U.S. Cl. ................................. 73/581; 73/862.41
[58] Field of Search .......................... 364/508; 73/579, 73/581, 652, 788, 862.41, 862.59, 862.391

[56] References Cited

U.S. PATENT DOCUMENTS

| | | | |
|---|---|---|---|
| 2,923,150 | 2/1960 | Imboden | 73/581 |
| 3,675,471 | 7/1972 | Bouche | 73/579 |
| 3,942,369 | 3/1976 | Roggenstein | 73/581 |
| 4,565,099 | 1/1986 | Arnold | 73/862.41 |
| 4,739,646 | 4/1988 | Van Brederode | 73/788 |
| 5,228,893 | 7/1993 | Smithgall | 73/581 |

*Primary Examiner*—Christine K. Oda
*Attorney, Agent, or Firm*—Otto M. Wildensteiner

[57] ABSTRACT

A method of determining the tension in a guy wire or other flexible member. The first 15 natural frequencies for the design tension and tensions at 1 percent increments above and below the design tension are calculated. The actual first 15 natural frequencies are then determined, and the tension in the wire is the one whose calculated frequencies are most similar to the actual frequencies. The method is sensitive enough to use the wind to excite the wire or it can be manually struck to produce vibrations.

5 Claims, 1 Drawing Sheet

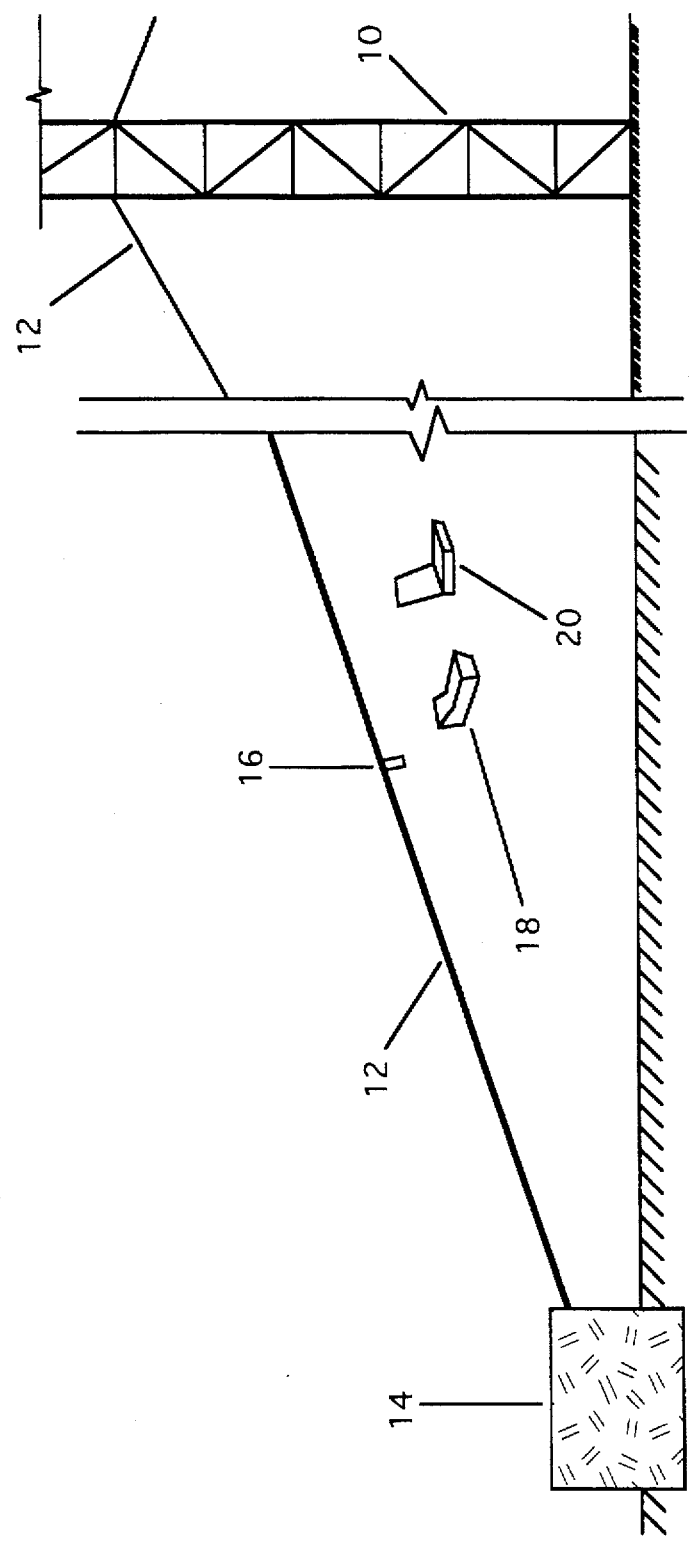

5,750,894

MEASUREMENT OF TENSION USING NATURAL FREQUENCY OF VIBRATION

STATEMENT OF GOVERNMENT INTEREST

The present invention may be made or used by or on behalf of the Government of the United States without the payment of any royalties thereon or therefor.

BACKGROUND

Tall towers, such as radio and television broadcasting towers, are supported by cables running from the tower to the ground called "guy" wires. These guy wires are on all sides of a tower and absorb the forces of winds, etc. on the tower. When a tower is designed it is designed as a unit which includes the guy wires and the tension in them. It is important that the tension in the wires be kept close to the design value, since a tension greater or lower than designed could allow the tower to bend and perhaps fail under high winds. Finally, uneven tension in the guy wires could distort the tower and make it susceptible to wind damage.

Present methods of determining guy wire tension are clumsy, time-consuming, dangerous, and/or inaccurate. One such method involves a device which puts a small flat "kink" in the wire; the amount of force required to put a given amount of kink in the wire is related to the tension in the wire by means of a calibration chart for that particular type of wire. This method is usable only on small wires with less than 5,000 pounds of tension in them. Further, frequent or improper use of this method can damage the wire.

Another method uses what are called "direct tension devices", which are mechanical or hydraulic devices that are in series or parallel with the wire whose tension is being measured. The force in the device is converted into guy wire tension by a calibration factor. This method can be used to measure tensions of up to 50,000 pounds. However, on large towers, because of the forces involved and the size and weight of the equipment required to measure such forces, this method involves considerable risk of danger to those doing the measuring. At the same time, however, this method is generally considered to be the most accurate (within 5%).

A third method, for wires having a tension of less than 5,000 pounds, involves imparting a pulse to the wire and then measuring the time it takes for the pulse to travel several times up and down the wire. The average time of travel per oscillation can then be converted to tension in the wire.

A fourth method, also for wires having tensions less than 5,000 pounds, involves pushing and pulling perpendicular to the wire to set it swaying like a pendulum. The average time per swing can then be converted to tension in the wire. Both of these latter methods have accuracies of 10% at best, and the presence of insulators on the wires significantly reduces the accuracy of the results in both cases.

OBJECTS OF THE INVENTION

Accordingly, it is an object of the present invention to provide a method of determining the tension in a flexible member that is simple and easily implemented.

It is a further object to provide such a method that requires very little instrumentation to implement.

It is a further object to provide such a method that provides greater accuracy than present methods.

It is a further object to provide such a method that is safer for use on members carrying large amounts of tension than present methods.

IN THE DRAWINGS

The only FIGURE shows the hardware used in the practice of the present invention.

SUMMARY

Briefly, the present invention is used to determine the tension in a flexible member using calculated and measured natural frequencies of vibration. The first fifteen natural frequencies of vibration for the flexible member at the design tension are calculated, as well as the first fifteen natural frequencies at tensions above and below the design value. The actual natural frequencies of the member are then measured with an accelerometer and FFT signal analyzer. Each actual natural frequency is compared to the corresponding calculated natural frequency at various tensions until the tension is found which provides the best match between the actual and calculated values for that natural frequency. Since each actual natural frequency can correspond to the calculated values, with interpolation, at a slightly different value of tension, the base tension for the guy wire is determined as the average of the tensions determined from each actual natural frequency. The tension in the wire increases with height above the ground due to the weight of the wire itself. Since it is easier to work at ground level rather than where the wire is attached to the tower, the tension that is usually determined is that at the base of the wire or "base tension".

DESCRIPTION OF THE PREFERRED EMBODIMENT

The FIGURE shows a portion of a guyed tower 10 and typical guy wire 12. Guy wire 12 is attached at its top end to tower 10 and at its base end to anchor block 14. In order to measure the natural frequency of vibration of wire 12 a small accelerometer 16 such as a Wilcoxon model 793L made by Wilcoxon Research, Gaithersburg, Md. is attached to wire 12, the output of which is fed to portable signal analyzer 18. Alternatively, any small or miniature accelerometer which provides "excellent" response down to 1 Hz and "good" response down to 0.1 Hz can be used.

Ordinarily, there is enough wind to cause wire 12 to vibrate sufficiently to get a usable output from accelerometer 16; if not, the wire can be struck with an object to make it vibrate.

The output from accelerometer 16 is collected for about 60 seconds by signal analyzer 18, such as a Hewlett Packard 3560A portable dual-channel dynamic signal analyzer. Signal analyzer 18 transforms the output of accelerometer 16 from time domain to frequency domain by Fast Fourier Transfer. As a result of this the natural frequencies are plainly evident as peaks in the power spectrum record, and the first 15 are recorded manually. Each of these first 15 actual natural frequencies is compared manually to the corresponding calculated natural frequency (see infra for the method of calculating the natural frequency) at various assumed tensions until the bracketing tensions are found which provide the best match between the actual and calculated values for that natural frequency. Each actual natural frequency, with linear interpolation between the bracketing tensions, will provide a slightly different value of tension. The tensions are stored on portable computer 20 and the final base tension in guy wire 12 is determined as the average of the interpolated base tensions from the 15 natural frequencies.

Fewer than the first 15 natural frequencies can be used, but with a corresponding decrease in accuracy. Likewise, more than 15 natural frequencies can be used but the increase in accuracy falls off rapidly beyond this number.

Calculated values of natural frequencies are obtained as follows: The horizontal span of the wire, the vertical span of the wire, the effective modulus of elasticity of the wire, the net cross-sectional area of the wire, the weight density of the wire material, the design base tension of the wire, and the weights and spacings of any insulators on the wire are input into the program of Appendix A. After the static properties of the entire guy wire are calculated, the wire is divided into hundreds of short segments. A matrix result is calculated from $\overline{K}-\lambda\overline{m}$. In this equation, $\overline{K}$ is a symmetric square global stiffness matrix which is generated from the exact stiffness of the elastic catenary guy wire segments, $\lambda$ is an Eigenvalue, and $\overline{m}$ is a symmetric square mass matrix. An Eigenvalue exists when the determinant of the above equation equals zero, and the square root of an Eigenvalue is a natural frequency.

The computer program in Appendix A, written in Fortran, calculates the static properties of the guy wire. Calculation of the natural frequencies requires knowing, in addition to the properties of the wire per se listed above, the values of the unstrained length of the guy wire, the tension at the base of the guy wire, and the horizontal and vertical components of the tension at the base of the wire. Usually only either the unstrained length of the wire or the base tension in the wire (i.e. the design tension) is known and the other must be solved for; the program of Appendix A calculates whichever of these is unknown.

Once these last properties are known, they are used in the program of Appendix B, written in Matlab, to calculate the natural frequencies of the wire. As stated earlier, in the beginning the tension at the base of the wire is assumed to be the design value and the first 15 natural frequencies are calculated for this value. Then the assumed tension is increased at 1% intervals for 20 intervals and decreased at 1% intervals for 20 intervals and 15 natural frequencies are calculated at each of these assumed tensions.

Data collection may require more than 60 seconds if the wind is gusting, since gusts tend to obscure the peaks in the output of accelerometer 16. Also, the present method is based on the assumption that the shape of the guy wire (i.e. a catenary) and the tension in the wire are the same whether the wind is blowing or calm. Therefore, when the wind speed is sufficient to change the shape of the wire and increase the load on the wire, above about 15 miles per hour, the accuracy of the present method decreases.

As a further refinement, the collection of data from accelerometer 16, the determination of the actual natural frequencies, and the calculation of base tension can be accomplished faster, automatically and more accurately with a portable computer 20 which has installed in it a credit card sized PCMCIA analog to digital converter such as a model DT7102 from Data Translation, Inc., Marlboro, Mass. The output from accelerometer 16 is fed to portable computer 20 via the PCMCIA analog-to-digital converter. A computer program (not provided, as portions of this program must be specifically compatible with the particular manufacturer's PCMCIA analog to digital converter) collects data for 5 seconds and the first 15 natural frequencies are determined and stored. While the program determines the frequencies for the first set of data, data is collected for 5 more seconds, the new data is added to the old, and the first 15 natural frequencies are again determined. This process of additional data collection and re-determination of the natural frequencies is repeated until 10 of the 15 most recently determined natural frequencies differ from the corresponding previous ones by 0.5% or less. The program then compares these 10 measured natural frequencies with the corresponding calculated values and a base tension is determined for each natural frequency. The final base tension is a weighted average of these tensions. The weighting factors are the percent differences between corresponding values in the last 2 rounds of measured natural frequencies.

In this refined version of the preferred embodiment, collecting data until 10 of the 15 measured natural frequencies converge within 0.5% will produce a result more quickly than if data were collected until all 15 natural frequencies converged, with very little sacrifice in accuracy of the final result. Also, determining the final base tension from the weighted average of 10 natural frequencies rather than the simple average of all 15 natural frequencies will produce a result more quickly and just as accurately as, if not more so than, the simple average of all 15 natural frequencies. Likewise, while it is preferred to keep re-determining the actual natural frequencies until 10 of a given set are within 0.5% of the corresponding ones of the previous set, it is possible to use fewer than 10 natural frequencies or to stop re-determining at a convergence of greater than 0.5%, but in both cases there will be a corresponding decrease in accuracy.

Although the present invention has been described in relation to a guy wire, it obviously can be used with any flexible member. For example, with only minor modifications to the computer programs it could be used to calculate the tension in the vertical cables in a suspension bridge.

APPENDIX A

Attachment B
FORTRAN source code for the calculation of static properties of a guy wire

```
        IMPLICIT REAL*12 (A-M,O-Z),  INTEGER*2 (N)
        INTEGER*2  Count,nToLo
        INTEGER*1  Pr
        DIMENSION PFData (500,2),PFDeck(20,3)
        CHARACTER*12 DataFileName
        CHARACTER*24 GuyName CALL OutWindowScroll (75)

*************************************************************************
*       DATA INPUT
*************************************************************************
        WRITE(*,*)'   This program solves the non-dimensional equations of the'
        WRITE(*,*)'   Elastic Catenary by use of a Newton-Rhapson routine. '
        WRITE(*,*)'  '
        WRITE(*,*)'   If Lo is known, then the program solves for H and V. If Lo is'
        WRITE(*,*)'   unknown then with Base tension (To) known, the program '
        WRITE(*,*)'   solves for H, V and Lo. For either case, a known weight of'
        WRITE(*,*)'   insulators can be either distributed uniformly along the'
        WRITE(*,*)'   unstrained length (Lo), or the user can input exact position '
        WRITE(*,*)'   and weight data for all the insulators and the program solves'
        WRITE(*,*)'   the problem as an Elastic Catenary with point loads.'
        WRITE(*,*)'  '
        WRITE(*,*)'   The program uses a columnar input file with the'
        WRITE(*,*)'   following variables:'
        WRITE(*,*)'   nFiles         number of files of data'
        WRITE(*,*)'   GuyName        up to 24 characters'
        WRITE(*,*)'   h              vertical guy span'
        WRITE(*,*)'   l              horizontal guy span'
        WRITE(*,*)'   E              modulus of Elasticity'
        WRITE(*,*)'   A              cross sectional area'
        WRITE(*,*)'   ins            weight of insulators (-1 to use point forces) '
        WRITE(*,*)'   Gamma          weight density of guy material'
        WRITE(*,*)'   nToLo          3 means To is known, 2 means Lo is known'
        WRITE(*,*)'   To     base tension'
        WRITE(*,*)'   Lo     unstrained guy length'
        WRITE(*,*)'   Tol            nondimensional calc tolerance (eg, 1e-10)'
        WRITE(*,*)'          NumCards     number of cards of point force input data'
        WRITE(*,*)'   Spacing,Number,Force           repeated NumCards times.'
        WRITE(*,*)'  '
        WRITE(*,*)'  '
        WRITE(*,*)'   Point force data is entered in cards. '
        WRITE(*,*)'   Each card has SPACING, NUMBER of repetitions and FORCE separated by commas.'
        WRITE(*,*)'   Ex: "36.4,5,50" generates five 50 lb forces spaced at 36.4 in.'
        WRITE(*,*)'   Also, set NumCards = 1 then 1,0,0 for ins >= 0'
        WRITE(*,*)'        There can be up to 20 cards and 500 forces.'
        WRITE(*,*)'   The locations of the point forces are measured along the unstrained guy'
        WRITE(*,*)'   beginning at the top guy anchor.'
        WRITE(*,*)'  '
        WRITE(*,*)'   units must be consistent for input variables'
        WRITE(*,*)'  '

WRITE(*,*)'   Enter data file name  (ccccccc.dat) '
        READ(6,10) DataFileName
10      FORMAT(A12)
        OPEN(10,FILE=DataFileName,Status='old')
        READ(10,*)nFiles
        WRITE(6,11) nFiles
11      FORMAT(5x,'There are ',i2,' files of data.')
        WRITE(*,*)'  '

DO 20 i=1,nFiles

SumForces       = 0
                NumForces       = 0
```

APPENDIX A

```
                    SumLength          = 0

READ(10,*) GuyName,h,l,E,A,Ins,Gamma,nToLo,To,Lo,Tol,NumCards
            DO 12 j=1,NumCards
                    READ(10,*) PFDeck(j,1),PFDeck(j,2),PFDeck(j,3)
                    SumForces      = SumForces + PFDeck(j,3)*PFDeck(j,2)
                    NumForces      = NumForces + PFDeck(j,2)
                    SumLength      = SumLength + PFDeck(j,1)*PFDeck(j,2)
12          CONTINUE
            WRITE(6,13) GuyName
13          FORMAT(5x,A24)
            WRITE(*,*)' '

CALL MMain (h,l,E,A,Ins,Gamma,nToLo,To,Lo,Tol,NumCards,SumForces,NumForces,PFDeck,Pr)

20      CONTINUE

REWIND(10)

END

SUBROUTINE MMain (h,l,E,A,Ins,Gamma,nToLo,To,Lo,Tol,NumCards,SumForces,NumForces,PFDeck,Pr)
***************************************************************
*       MAIN PROGRAM
***************************************************************
        IMPLICIT REAL*12 (A-M,O-Z),   INTEGER*2 (N)
        INTEGER*2  Count,nToLo
        INTEGER*1 Pr
        DIMENSION PFData (500,2),PFDeck(20,3)
        CHARACTER*12 DataFileName Chord      = SQRT(h2 + l2)
        EA         = E * A IF (INS.EQ.-1) THEN
*       Solution WITH POINT FORCES

*           Generate PFData from PFDeck
                Count       = 0
                s           = 0

DO 1010 i=1,NumCards
                DO 1020 j=1,PFDeck(i,2)
                    Count               = Count + 1
                    s                   = s + PFDeck(i,1)
                    PFData(Count,1)     = s
                    PFData(Count,2)     = PFDeck(i,3)
1020            CONTINUE
1010        CONTINUE Pr   = 1

IF (nToLo.eq.3) THEN
*               Estimate HH, V and Lo
                    Rho            = A * Gamma + SumForces/Chord
                    RhoTemp    = 0
                    HHo            = To*l/Chord
                    Weighto    = Rho * Chord
                    Vo             = To*h/Chord + Weighto
                    Pr = 2

DO WHILE ((abs(RhoTemp - Rho).gt.Tol))

RhoTemp    = Rho

CALL ThD (h,l,A,To,Tol,EA,Rho,HHo,Weighto,Vo,Pr,HH,V,Ttop,Lo,Weight)

Rho        = A * Gamma + SumForces / Lo
                        HHo        = HH
```

*APPENDIX A*

```
                    Vo          = V
                    Weighto     = Weight
            END DO Pr = 1

Rho    = A * Gamma

CALL ThDForces (h,l,A,To,Tol,NumForces,PFData,SumForces, Rho,EA,Pr, HH,V,Ttop,Lo,Weight)

ELSE
*       Estimate HH and V
        Rho         = A * Gamma + SumForces/Lo
        Weight   = Rho * Lo
        Pr = 2
        Ho = Weight
        Vo = Weight
        CALL TwD (h,l,A,Tol,EA,HH,V,To,Ttop,Lo,Weight,Pr,Ho,Vo)
        Rho         = A * Gamma
        Pr = 1
        CALL TwDForces (h,l,A,Lo,Rho,Tol,NumForces,PFData,SumForces,EA,Pr,HH,V,To,Ttop)

ENDIF

ELSE
*   Solution WITH UNIFORMLY DISTRIBUTED WEIGHT

IF (nToLo.eq.3) THEN
            RhoTemp    = 0
            Rho        = A * Gamma + Ins/Chord
            HHo        = To*l/Chord
            Weighto  = Rho * Chord
            Vo         = To*abs(h)/Chord + Weighto
            Pr = 2

DO WHILE ((abs(RhoTemp - Rho).gt.Tol))

RhoTemp    = Rho

CALL ThD (h,l,A,To,Tol,EA,Rho,HHo,Weighto,Vo,Pr,HH,V,Ttop,Lo,Weight)

Rho        = A * Gamma + Ins / Lo
            HHo        = HH
            Vo         = V
            Weighto    = Weight

END DO

WRITE(6,*)' '
        WRITE(6,1003)HH,Ttop,StrTop,Weight
1003    FORMAT(5X,' H    = ',F10.3,' lb',3x,' Ttop = ',F10.3,' lb',3x,' StrTop = ',F10.3,' psi',3x,' Weight =
            ',F10.3,' lb')
        WRITE(6,1004)V,To,StrBot,Lo
1004    FORMAT(5X,' V    = ',F10.3,' lb',3x,' To   = ',F10.3,' lb',3x,' StrBot = ',F10.3,' psi',3x,' Lo    =
            ',F12.5,' in')

ELSE
        Rho        = A * Gamma + Ins/Lo
        Weight   = Rho * Lo
        Pr = 1
        Ho = Weight
        Vo = Weight
        CALL TwD (h,l,A,Tol,EA,HH,V,To,Ttop,Lo,Weight,Pr,Ho,Vo)

ENDIF

ENDIF
```

```
      RETURN
      END

SUBROUTINE ThD (h,l,A,To,Tol, EA,Rho,HHo,Weighto,Vo,Pr, HH,V,Ttop,Lo,Weight)
***********************************************************************************
*     SUBROUTINE ThD SOLVES THE EQUATIONS OF THE ELASTIC CATENARY FOR H, V AND Lo
***********************************************************************************

IMPLICIT REAL*12 (A-M,O-Z),   INTEGER*2 (N)
      INTEGER*2 Count
      INTEGER*1 Pr

*     The non-dimensional constants for the subprogram are the following:
      eps        = To/EA
      lhat       = Rho*l/To
      hhat       = Rho*h/To

*     The initial values (guesses) at the non-dimensional subprogram variables are as follows:
      x    =      HHo/To
      z    =      Vo/To
      w    =      Weighto/To

*     The starting values for the remainders of the three non-dimensional equations are as follows:
      rlhat  = eps * w * x     + x * ( log(z/x + SQRT((z/x)**2 + 1)) - log((z-w)/x + SQRT(((z-w)/x)**2 + 1))) - lhat
      rhhat  = eps * w * (z - w/2)  + x * ( SQRT((z/x)**2+1) - SQRT(((z-w)/x)**2 + 1)) - hhat
      rThat  = SQRT(x2 + (z - w)2) - 1

*     Initialize internal subprogram variables to zero
      count = 0
      lhatx = 0
      lhatz = 0
      lhatw = 0
      hhatx = 0
      hhatz = 0
      hhatw = 0
      Thatx = 0
      Thatz = 0
      Thatw = 0
      DET   = 0
      delx  = 0
      delz  = 0
      delw  = 0

DO WHILE ((abs(rlhat).gt.tol).or.(abs(rhhat).gt.tol).or.(abs(rthat).gt.tol))

count = count + 1

*     This portion calculates the partial derivatives of lhat, hhat and That with respect to x, z, and w
          lhatx = eps *  w       + log(z/x + SQRT((z/x)**2 + 1)) - log((z-w)/x + SQRT(((z-w)/x)**2 + 1)) -
                 (z/x)/SQRT((z/x)**2 + 1) + ((z-w)/x)/SQRT(((z-w)/x)**2 + 1)
          lhatz =      1/SQRT((z/x)**2 + 1)    -    1/SQRT(((z-w)/x)**2 + 1)
          lhatw = eps * x    + 1/SQRT(((z-w)/x)**2 + 1)

hhatx = lhatz
          hhatz = eps *  w +  (z/x)/SQRT((z/x)**2 + 1)- ((z-w)/x)/SQRT(((z-w)/x)**2 + 1)
          hhatw = eps * (z-w) +  ((z-w)/x)/SQRT(((z-w)/x)**2 + 1)

Thatx =    1/SQRT(((z-w)/x)**2 + 1)
          Thatz =    ((z-w)/x)/SQRT(((z-w)/x)**2 + 1)
          Thatw = -  ((z-w)/x)/SQRT(((z-w)/x)**2 + 1)

*     This calculates the determinant of the flexibility matrix
          DET   = (-hhatz*lhatw + hhatw*lhatz)*Thatx - (-Thatz*lhatw + Thatw*lhatz)*hhatx + (-Thatz*hhatw +
                  Thatw*hhatz)*lhatx

*     This portion calculates the increments for x, z and w
```

APPENDIX A
Attachment B Page 4

```
          delx   = -1/DET * ( ( (-Thatz*hhatw + Thatw*hhatz) * rlhat + ( Thatz*lhatw - Thatw*lhatz) * rhhat + (-hhatz*lhatw +
                     hhatw*lhatz) * rThat)
          delz   = -1/DET * ( ( Thatx*hhatw - Thatw*hhatx) * rlhat + (-Thatx*lhatw + Thatw*lhatx) * rhhat + ( hhatx*lhatw -
                     hhatw*lhatx) * rThat)
          delw  = -1/DET * ( ( Thatz*hhatx - Thatx*hhatz) * rlhat + (-Thatz*lhatx + Thatx*lhatz) * rhhat + ( hhatz*lhatx -
                     hhatx*lhatz) * rThat)

IF (x+delx.ge.1) THEN
                  x = 0.99999999
          ELSE
                  x = x + delx
          ENDIF
          z      = z + delz
          w      = w + delw

*    This calculates the remainder of the lhat, hhat and That equations based on the new values of x, z, and w
          rlhat  = eps * w * x          + x * ( log(z/x + SQRT((z/x)**2 + 1)) - log((z-w)/x + SQRT(((z-w)/x)**2 + 1))) - lhat
          rhhat  = eps * w * (z - w/2)  + x * ( SQRT((z/x)**2+1) - SQRT(((z-w)/x)**2 + 1)) - hhat
          rThat  = SQRT(x2 + (z - w)2) - 1

END DO

*    calculate the actual values of H, V, Weight and Lo
          HH      = x * To
          V       = z * To
          Weight  = w * To
          Lo      = Weight / Rho
          Ttop    = (V**2 + HH**2)**.5
          StrTop  = Ttop/A
          StrBot  = To/A IF (Pr.EQ.1) THEN
                  WRITE(6,302)count
302              FORMAT(4X,'After ',I3,' iterations')
                  WRITE(6,*)' '
                  WRITE(6,303)HH,Ttop,StrTop,Weight
303              FORMAT(5X,' H     = ',F10.3,'  lb',3x,' Ttop   = ',F10.3,'  lb',3x,' StrTop = ',F10.3,'  psi',3x,' Weight =
                     ',F10.3,'  lb')
                  WRITE(6,304)V,To,StrBot,Lo
304              FORMAT(5X,' V     = ',F10.3,'  lb',3x,' To     = ',F10.3,'  lb',3x,' StrBot = ',F10.3,'  psi',3x,' Lo     =
                     ',F12.5,'  in')

ENDIF

RETURN
          END
          SUBROUTINE TwD (h,l,A,Tol,EA,HH,V,To,Ttop,Lo,Weight,Pr,Ho,Vo)
***********************************************************************************************
*    SUBROUTINE TwD SOLVES THE EQUATIONS OF THE ELASTIC CATENARY FOR H AND V
***********************************************************************************************

IMPLICIT REAL*12 (A-M,O-Z),   INTEGER*2 (N)
          INTEGER*2 Count
          INTEGER*1 Pr

*    Non-dimensional subprogram constants
          eps     = Weight/EA
          lhat    =    l/Lo
          hhat    =    h/Lo

*    Non-dimensional subprogram variables
          x       =    Ho/Weight
          z       =    Vo/Weight

*    The starting values for the remainders of the two non-dimensional equations are as follows:
          rlhat  = eps * x          + x * ( log(z/x + SQRT((z/x)**2 + 1)) - log((z-1)/x + SQRT(((z-1)/x)**2 + 1))) - lhat
          rhhat  = eps * (z-0.5)    + x * ( SQRT( (z/x)**2 + 1) - SQRT( ((z-1)/x)**2 + 1 )) - hhat
```

APPENDIX A
Page 5

CG 96-3

* Initialize internal subprogram variables to zero
  ```
  count = 0
  lhatx = 0
  lhatz = 0
  hhatx = 0
  hhatz = 0
  DET  = 0
  delx = 0
  delz = 0
  ```

DO WHILE ((abs(rlhat).gt.Tol).or.(abs(rhhat).gt.Tol))

count = count + 1

* This portion calculates the partial derivatives of lhat and hhat with respect to x and z
  $$\text{lhatx} = \text{eps} + \log(z/x + \text{SQRT}((z/x)^{}2 + 1)) - \log((z-1)/x + \text{SQRT}(((z-1)/x)^{}2 + 1)) - (z/x)/\text{SQRT}((z/x)^{}2 + 1) + ((z-1)/x)/\text{SQRT}(((z-1)/x)^{}2 + 1)$$
  $$\text{lhatz} = 1/\text{SQRT}((z/x)^{}2 + 1) - 1/\text{SQRT}(((z-1)/x)^{}2 + 1)$$

hhatx = lhatz
  $$\text{hhatz} = \text{eps} + (z/x)/\text{SQRT}((z/x)^{}2 + 1) - ((z-1)/x)/\text{SQRT}(((z-1)/x)^{}2 + 1)$$

* This calculates the determinant of the flexibility matrix
  DET = lhatx*hhatz-hhatx*lhatz

* This portion calculates the increments for x and z
  delx = -1/DET * ( hhatz * rlhat - lhatz * rhhat )
  delz = -1/DET * ( -hhatx * rlhat + lhatx * rhhat )

```
  IF (x+delx.lt.0) THEN
          x = 0.00001
      ELSE
          x = x + delx
  ENDIF IF (z+delz.lt.0) THEN
          z = 0.00001
      ELSE
          z = z + delz
  ENDIF
  ```

* This calculates the remainder of the lhat and hhat equations based on the new values of x and z
  rlhat = eps * x + x * ( log(z/x + SQRT((z/x)2 + 1)) - log((z-1)/x + SQRT(((z-1)/x)2 + 1)) ) - lhat
  rhhat = eps * (z-0.5) + x * ( SQRT( (z/x)2 + 1 ) - SQRT( ((z-1)/x)2 + 1 ) ) - hhat

END DO

* This portion calculates the actual values of H and V
  ```
  HH     = x * Weight
  V      = z * Weight
  Ttop   = (V**2 + HH**2)**.5
  To     = ((V-Weight)**2 + HH**2)**.5
  StrTop = Ttop/A
  StrBot = To/A
  ```

IF (Pr.EQ.1) THEN
      WRITE(6,602)count
  602    FORMAT(4X,'After ',I3,' iterations')
      WRITE(6,*) ' '
      WRITE(6,603)HH,Ttop,StrTop,Weight
  603    FORMAT(5X,' H   = ',F10.3,' lb',3x,' Ttop   = ',F10.3,' lb',3x,' StrTop = ',F10.3,' psi',3x,' Weight = ',F10.3,' lb')
      WRITE(6,604)V,To,StrBot,Lo
  604    FORMAT(5X,' V   = ',F10.3,' lb',3x,' To   = ',F10.3,' lb',3x,' StrBot = ',F10.3,' psi',3x,' Lo   = ',F12.5,' in')

ENDIF

APPENDIX A

```
        RETURN
        END

SUBROUTINE ThDForces (h,l,A,To,Tol,NumForces,PFData,SumForces, Rho,EA,Pr, HH,V,Ttop,Lo,Weight)
*****************************************************************************************************
*       SUBROUTINE ThDForces SOLVES THE EQUATIONS OF THE ELASTIC CATENARY FOR H,V and Lo
*       when there are a known number of point forces
*****************************************************************************************************

IMPLICIT REAL*12 (A-M,O-Z),    INTEGER*2 (N)
        INTEGER*2 Count,i,j
        INTEGER*1 Pr
        DIMENSION PFData (500,2)

*       The non-dimensional constants for the subprogram are the following:
        eps       =   To/EA
        lhat      =   Rho*l/To
        hhat      =   Rho*h/To
        SumPhi    =   SumForces/To

*       The initial values (guesses) at the non-dimensional subprogram variables are as follows:
        x         =   HH/To
        z         =   V/To
        w         =   Rho*Lo/To SinhConstant = 0
        SQRTConstant = 0
        zwxOverSQRTC = 0
        OneOverSQRTC = 0
        SumPhiiwi    = 0
        SumPhiiOne   = 0
        SumPhiiTwo   = 0

*       The starting values for the remainders of the three non-dimensional equations are as follows:
        DO 333 i=1,NumForces wi                 = Rho   * PFData(i,1)/To
                SumPhiiOne         = SumPhiiOne + PFData(i,2)/To SinhConstant = SinhConstant +  log( (z-wi-SumPhiiOne)/x + SQRT(((z-wi-SumPhiiOne)/x)**2 + 1) ) - log( (z-wi-
                        SumPhiiTwo)/x + SQRT(((z-wi-SumPhiiTwo)/x)**2 + 1) )
                SQRTConstant = SQRTConstant +  SQRT( ((z-wi-SumPhiiOne)/x)**2 + 1 ) - SQRT( ((z-wi-SumPhiiTwo)/x)**2
                        + 1)
                zwxOverSQRTC = zwxOverSQRTC + ((z-wi-SumPhiiOne)/x)/SQRT(((z-wi-SumPhiiOne)/x)**2 + 1) - ((z-wi-
                        SumPhiiTwo)/x)/SQRT(((z-wi-SumPhiiTwo)/x)**2 + 1)
                OneOverSQRTC = OneOverSQRTC +  1/SQRT(((z-wi-SumPhiiOne)/x)**2 + 1) - 1/SQRT(((z-wi-
                        SumPhiiTwo)/x)**2 + 1)
                SumPhiiwi    = SumPhiiwi    + wi * PFData(i,2)/To SumPhiiTwo         = SumPhiiOne

333     CONTINUE rlhat   = eps * w * x  + x * ( log(z/x + SQRT((z/x)2 + 1)) - log((z-w-SumPhi)/x + SQRT(((z-w-SumPhi)/x)2 + 1)))
                  + x * SinhConstant - lhat
        rhhat   = eps * w * (z - w/2 - SumPhi) - eps * SumPhiiwi   + x * ( SQRT((z/x)**2+1) - SQRT(((z-w-SumPhi)/x)**2 +
                    1)) + x * SQRTConstant - hhat
        rThat   = SQRT(x**2 + (z - w - SumPhi)**2) - 1

*       Initialize internal subprogram variables to zero
        count = 0
        lhatx = 0
        lhatz = 0
```

APPENDIX A

```
lhatw = 0
hhatx = 0
hhatz = 0
hhatw = 0
Thatx = 0
Thatz = 0
Thatw = 0
DET  = 0
delx = 0
delz = 0
delw = 0
```

DO WHILE ((abs(rlhat).gt.Tol).or.(abs(rhhat).gt.Tol).or.(abs(rThat).gt.Tol))

count = count + 1

* This portion calculates the partial derivatives of lhat, hhat and That with respect to x, z, and w

```
lhatx = eps*w + log(z/x + SQRT((z/x)**2 + 1)) - log((z-w-SumPhi)/x + SQRT(((z-w-SumPhi)/x)**2 + 1)) -
        (z/x)/SQRT((z/x)**2 + 1) + ((z-w-SumPhi)/x)/SQRT(((z-w-SumPhi)/x)**2 + 1) + SinhConstant -
        zwxOverSQRTC
lhatz =      1/SQRT((z/x)**2 + 1)  - 1/SQRT(((z-w-SumPhi)/x)**2 + 1) + OneOverSQRTC
lhatw = eps *  x+1/SQRT(((z-w-SumPhi)/x)**2 + 1) - OneOverSQRTC hhatx = lhatz
hhatz = eps *w + (z/x)/SQRT((z/x)2 + 1)- ((z-w-SumPhi)/x)/SQRT(((z-w-SumPhi)/x)2 + 1) +
        zwxOverSQRTC
hhatw = eps * (z-w-SumPhi) +  ((z-w-SumPhi)/x)/SQRT(((z-w-SumPhi)/x)2 + 1) - zwxOverSQRTC Thatx =1/SQRT(((z-w-SumPhi)/x)2 + 1)
Thatz =((z-w-SumPhi)/x)/SQRT(((z-w-SumPhi)/x)**2 + 1)
Thatw = -  ((z-w-SumPhi)/x)/SQRT(((z-w-SumPhi)/x)**2 + 1)
```

* This calculates the determinant of the flexibility matrix
    DET  = (-hhatz*lhatw + hhatw*lhatz)*Thatx - (-Thatz*lhatw + Thatw*lhatz)*hhatx + (-Thatz*hhatw +
           Thatw*hhatz)*lhatx

* This portion calculates the increments for x, z and w
    delx  = -1/DET * ( (-Thatz*hhatw + Thatw*hhatz) * rlhat + ( Thatz*lhatw - Thatw*lhatz) * rhhat + (-hhatz*lhatw +
            hhatw*lhatz) * rThat)
    delz  = -1/DET * ( ( Thatz*hhatw - Thatw*hhatx) * rlhat + (-Thatx*lhatw + Thatw*lhatx) * rhhat + ( hhatx*lhatw -
            hhatw*lhatx) * rThat)
    delw  = -1/DET * ( ( Thatz*hhatx - Thatx*hhatz) * rlhat + (-Thatz*lhatx + Thatx*lhatz) * rhhat + ( hhatz*lhatx -
            hhatx*lhatz) * rThat)

IF (x+delx.ge.1) THEN
        x = 0.99999999
    ELSE
        x = x + delx
    ENDIF
    z    = z + delz
    w    = w + delw

* This calculates the remainder of the lhat, hhat and That equations based on the new values of x, z, and w

```
SinhConstant = 0
SQRTConstant = 0
zwxOverSQRTC = 0
OneOverSQRTC = 0
SumPhiiwi  = 0
SumPhiiOne = 0
SumPhiiTwo = 0
```

DO 335 i=1,NumForces

```
wi          = Rho   * PFData(i,1)/To
SumPhiiOne  = SumPhiiOne + PFData(i,2)/To
```

APPENDIX A
Page 8

```
            SinhConstant = SinhConstant + log( (z-wi-SumPhiiOne)/x + SQRT(((z-wi-SumPhiiOne)/x)**2 + 1) ) - log( (z-wi-
                           SumPhiiTwo)/x + SQRT(((z-wi-SumPhiiTwo)/x)**2 + 1) )
            SQRTConstant = SQRTConstant + SQRT( ((z-wi-SumPhiiOne)/x)**2 + 1 ) - SQRT( ((z-wi-SumPhiiTwo)/x)**2
                           + 1)
            zwxOverSQRTC = zwxOverSQRTC + ((z-wi-SumPhiiOne)/x)/SQRT(((z-wi-SumPhiiOne)/x)**2 + 1) - ((z-wi-
                           SumPhiiTwo)/x)/SQRT(((z-wi-SumPhiiTwo)/x)**2 + 1)
            OneOverSQRTC = OneOverSQRTC + 1/SQRT(((z-wi-SumPhiiOne)/x)**2 + 1) - 1/SQRT(((z-wi-
                           SumPhiiTwo)/x)**2 + 1)
            SumPhiiwi    = SumPhiiwi    + wi * PFData(i,2)/To SumPhiiTwo = SumPhiiOne

335   CONTINUE rlhat  = eps * w * x  + x * ( log(z/x + SQRT((z/x)2 + 1)) - log((z-w-SumPhi)/x + SQRT(((z-w-SumPhi)/x)2 + 1))
             + x * SinhConstant - lhat
      rhhat  = eps * w * (z - w/2 - SumPhi) - eps * SumPhiiwi  + x * ( SQRT((z/x)**2+1) - SQRT(((z-w-SumPhi)/x)**2 +
                           1)) + x * SQRTConstant - hhat
      rThat  = SQRT(x**2 + (z - w - SumPhi)**2) - 1

END DO

*     This portion calculates the actual values of H, V, Weight and Lo
      HH        = x * To
      V         = z * To
      Weight    = w * To
      Lo        = Weight / Rho
      Weight    = Weight + SumForces
      Ttop      = SQRT(V**2 + HH**2)
      ToCh      = SQRT((V-Weight-SumForces)**2 + HH**2)
      StrTop = Ttop/A
      StrBot =  To/A IF (Pr.EQ.1) THEN
            WRITE(6,302)count
302         FORMAT(4X,'After ',I3,' iterations')
            WRITE(6,*)' '
            WRITE(6,303)HH,Ttop,StrTop,Weight
303         FORMAT(5X,' H    = ',F10.3, ' lb',3x,' Ttop  = ',F10.3, ' lb',3x,' StrTop = ',F10.3, ' psi',3x,' Weight =
                   ',F10.3, ' lb')
            WRITE(6,304)V,ToCh,StrBot,Lo
304         FORMAT(5X,' V    = ',F10.3, ' lb',3x,' ToCh  = ',F10.3, ' lb',3x,' StrBot = ',F10.3, ' psi',3x,' Lo
                   = ',F12.5, ' in')

ENDIF

RETURN
      END

SUBROUTINE TwDForces (h,l,A,Lo,Rho,Tol,NumForces,PFData,SumForces, EA,Pr, HH,V,To,Ttop)
***************************************************************************************************
*     SUBROUTINE TwDForces SOLVES THE EQUATIONS OF THE ELASTIC CATENARY FOR H and V
*     when there are a known number of point forces
***************************************************************************************************

IMPLICIT REAL*12 (A-M,O-Z),    INTEGER*2 (N)
      INTEGER*2 Count,i,j
      INTEGER*1 Pr
      DIMENSION PFData (500,2)

Weight    =    Rho * Lo

*     The non-dimensional constants for the subprogram are the following:
      eps       =    Weight/EA
      lhat      =    l/Lo
      hhat      =    h/Lo
```

SumPhi       = SumForces/Weight

* The initial values (guesses) at the non-dimensional subprogram variables are as follows:
  x  =  HH/Weight
  z  =  V/Weight

```
SinhConstant = 0
SQRTConstant = 0
zsxOverSQRTC = 0
OneOverSQRTC = 0
SumSigmaPhii = 0
SumPhiiOne   = 0
SumPhiiTwo   = 0
```

* The starting values for the remainders of the two non-dimensional equations are as follows:
  DO 334 i=1,NumForces sigmai     = PFData(i,1)/Lo
  SumPhiiOne = SumPhiiOne + PFData(i,2)/Weight SinhConstant = SinhConstant + log( (z-sigmai-SumPhiiOne)/x + SQRT(((z-sigmai-SumPhiiOne)/x)**2 + 1) ) -
                 log( (z-sigmai-SumPhiiTwo)/x + SQRT(((z-sigmai-SumPhiiTwo)/x)**2 + 1) )
  SQRTConstant = SQRTConstant + SQRT( ((z-sigmai-SumPhiiOne)/x)**2+1 )-SQRT( ((z-sigmai-
                 SumPhiiTwo)/x)**2 + 1)
  zsxOverSQRTC = zsxOverSQRTC + ((z-sigmai-SumPhiiOne)/x)/SQRT(((z-sigmai-SumPhiiOne)/x)**2 + 1) - ((z-
                 sigmai-SumPhiiTwo)/x)/SQRT(((z-sigmai-SumPhiiTwo)/x)**2 + 1)
  OneOverSQRTC = OneOverSQRTC + 1/SQRT(((z-sigmai-SumPhiiOne)/x)**2 + 1) - 1/SQRT(((z-sigmai-
                 SumPhiiTwo)/x)**2 + 1)
  SumSigmaPhii = SumSigmaPhii + Sigmai * PFData(i,2)/Weight SumPhiiTwo = SumPhiiOne

334 CONTINUE rlhat  = eps * x  + x * ( log(z/x + SQRT((z/x)2 + 1)) - log((z-1-SumPhi)/x + SQRT(((z-1-SumPhi)/x)2 + 1))) + x *
           SinhConstant - lhat
  rhhat  = eps * (z - 0.5 - SumPhi - SumSigmaPhii)  + x * ( SQRT((z/x)2+1) - SQRT(((z-1-SumPhi)/x)2 + 1)) + x *
           SQRTConstant - hhat

* Initialize internal subprogram variables to zero
  count = 0
  lhatx = 0
  lhatz = 0
  hhatx = 0
  hhatz = 0
  DET   = 0
  delx  = 0
  delz  = 0

DO WHILE ((abs(rlhat).gt.Tol).or.(abs(rhhat).gt.Tol))

count = count + 1

* This portion calculates the partial derivatives of lhat and hhat with respect to x and z
  lhatx = eps + log(z/x + SQRT((z/x)2 + 1)) - log((z-1-SumPhi)/x + SQRT(((z-1-SumPhi)/x)2 + 1)) -
          (z/x)/SQRT((z/x)2 + 1) + ((z-1-SumPhi)/x)/SQRT(((z-1-SumPhi)/x)2 + 1) + SinhConstant -
          zsxOverSQRTC
  lhatz = 1/SQRT((z/x)2 + 1)  - 1/SQRT(((z-1-SumPhi)/x)2 + 1) + OneOverSQRTC hhatx = lhatz
  hhatz = eps + (z/x)/SQRT((z/x)2 + 1)  - ((z-1-SumPhi)/x)/SQRT(((z-1-SumPhi)/x)2 + 1) +
          zsxOverSQRTC

* This calculates the determinant of the flexibility matrix
  DET   = lhatx*hhatz-hhatx*lhatz APPENDIX A
Page 10

\* This portion calculates the increments for x and z

```
        delx  = -1/DET * ( hhatz * rlhat - lhatz * rhhat )
        delz  = -1/DET * ( -hhatx * rlhat + lhatx * rhhat )

IF (x+delx.lt.0) THEN
                    x = 0.00001
              ELSE
                    x = x + delx
              ENDIF IF (z+delz.lt.0) THEN
                    z = 0.00001
              ELSE
                    z = z + delz
              ENDIF
```

\* This calculates the remainder of the lhat and hhat equations based on the new values of x and z

```
        SinhConstant = 0
        SQRTConstant = 0
        zsxOverSQRTC = 0
        OneOverSQRTC = 0
        SumSigmaPhii = 0
        SumPhiiOne  = 0
        SumPhiiTwo  = 0

DO 336 i=1,NumForces sigmai    = PFData(i,1)/Lo
              SumPhiiOne = SumPhiiOne + PFData(i,2)/Weight SinhConstant = SinhConstant + log( (z-sigmai-SumPhiiOne)/x + SQRT(((z-sigmai-SumPhiiOne)/x)**2 + 1) ) -
                              log( (z-sigmai-SumPhiiTwo)/x + SQRT(((z-sigmai-SumPhiiTwo)/x)**2 + 1) )
              SQRTConstant = SQRTConstant + SQRT( ((z-sigmai-SumPhiiOne)/x)**2 + 1 ) - SQRT( ((z-sigmai-
                              SumPhiiTwo)/x)**2 + 1)
              zsxOverSQRTC = zsxOverSQRTC + ((z-sigmai-SumPhiiOne)/x)/SQRT(((z-sigmai-SumPhiiOne)/x)**2 + 1) - ((z-
                              sigmai-SumPhiiTwo)/x)/SQRT(((z-sigmai-SumPhiiTwo)/x)**2 + 1)
              OneOverSQRTC = OneOverSQRTC + 1/SQRT(((z-sigmai-SumPhiiOne)/x)**2 + 1) - 1/SQRT(((z-sigmai-
                              SumPhiiTwo)/x)**2 + 1)
              SumSigmaPhii = SumSigmaPhii + Sigmai * PFData(i,2)/Weight SumPhiiTwo = SumPhiiOne

336     CONTINUE rlhat = eps * x + x * ( log(z/x + SQRT((z/x)2 + 1)) - log((z-1-SumPhi)/x + SQRT(((z-1-SumPhi)/x)2 + 1))) + x *
                      SinhConstant - lhat
        rhhat = eps * (z - 0.5 - SumPhi - SumSigmaPhii) + x * ( SQRT((z/x)**2+1) - SQRT(((z-1-SumPhi)/x)**2 + 1)) + x *
                      SQRTConstant - hhat

END DO
```

\* This portion calculates the actual values of H and V

```
        HH       = x * Weight
        V        = z * Weight
        Ttop     = (V**2 + HH**2)**.5
        To       = ((V-Weight-SumForces)**2 + HH**2)**.5
        Weight   = Weight + SumForces
        StrTop   = Ttop/A
        StrBot   = To/A IF (Pr.EQ.1) THEN
              WRITE(6,602)count
602           FORMAT(4X,'After ',I3,' iterations')
              WRITE(6,*)' '
              WRITE(6,603)HH,Ttop,StrTop,Weight
603           FORMAT(5X,' H   = ',F10.3,' lb',3x,' Ttop = ',F10.3,' lb',3x,' StrTop = ',F10.3,' psi',3x,' Weight =
                            ',F10.3,' lb')
```

```
        WRITE(6,604)V,To,StrBot,Lo
604     FORMAT(5X,' V     = ',F10.3,'  lb',3x,' To    = ',F10.3, '  lb',3x,' StrBot = ',F10.3, '  psi',3x,' Lo   =
        ',F12.5,'  in')
ENDIF

RETURN
END
```

Appendix D
~~Attachment C~~
Matlab source code for calculation of guy wire natural frequencies

```
h=1200;l=4200;E=23000000;A=0.1145;L=4365.9989;Tb=2310;W=243.1276;
H=2060.7729;V=743.8436;
nins=7;
ins=[16 66 106 166 216 266 316;75 8 8 8 8 8 8];
sumins=(6*8+75);
W=W-sumins;
Rho=W/L;Mass=W/386.4;
% n is the number of cable segments and nn is the number of DOF
n=5;
% numLLs is the number of Eigenvalues to be calculated
numLLs=4;

%call Kandm subroutine
Kandm;

%GUESS AT LLAMBDA AND CALCULATE (NORMALIZED) K-LL*M
Pendulumsquared=pi^2/l^2*(H*L/(Mass*sqrt(1+(h/l)^2)));
LL=2*Pendulumsquared;
inc=LL;
iteration=1;
data=zeros(2*numLLs,3);
nneg=0;
nnegt1=0;
LLt1=LL;
dett1=0;

%call subroutine a=k-LL*m
kminusLLxm;
%call subroutine to calc determinant and # of neg diagonal numbers
detandnneg;

LLt1 =LL;
nnegt1=nneg;
dett1 =determinant;

inc=2*Pendulumsquared;

%step along determinant function and bound eigenvalues
while nneg<(numLLs+1)
   inc1=inc;
  if nnegt1==nneg;
dett1=determinant;
   LL=LL+inc1;
   kminusLLxm;
   detandnneg;
  elseif nneg-nnegt1==1
   data(iteration,1)=LL-inc;
   data(iteration,2)=dett1;
```

Appendix D
~~Attachment C~~ Page 1

```
    data(iteration,3)=nnegt1;
    iteration=iteration+1;
    data(iteration,1)=LL;
    data(iteration,2)=determinant;
    data(iteration,3)=nneg;
 nnegt1=nneg;
    iteration=iteration+1;
  else nnegt1-nneg>1;
    LL=LL-inc1;
    inc1=inc1/2;
    nnegt1=nneg;
  end
end
format short
data %zoom to eigenvalues by factor of 4 with bisection
% so as to ensure convergence w/secant search
for iii=1:numLLs
  LL1=data(2*iii-1,1);
  LL2=data(2*iii,1);
  d1 =data(2*iii-1,2);
  d2 =data(2*iii,2);
  LL=(LL1+LL2)/2;
kminusLLxm;
  detandnneg;

if nneg==data(2*iii-1,3)
    data(2*iii-1,1)=LL;
data(2*iii-1,2)=determinant;
    LL=(LL+data(2*iii,1))/2;
  kminusLLxm;
    detandnneg;
    if nneg==data(2*iii-1,3)
      data(2*iii-1,1)=LL;
    data(2*iii-1,2)=determinant;
    else
      data(2*iii,1)=LL;
    data(2*iii,2)=determinant;
    end
  else
   data(2*iii,1)=LL;
   data(2*iii,2)=determinant;
   LL=(LL+data(2*iii-1,1))/2;
  kminusLLxm;
    detandnneg;
   if nneg==data(2*iii,3)
     data(2*iii,1)=LL;
   data(2*iii,2)=determinant;
   else
     data(2*iii-1,1)=LL;
   data(2*iii-1,2)=determinant;
   end
end
```

```
end
format short
data

%secant search to converge to eigenvalues
 Freq=zeros(numLLs,3);
 eta=1;
for i4=1:numLLs
 LL1=data(2*i4-1,1);
 LL2=data(2*i4,1);
 d1 =data(2*i4-1,2);
 d2 =data(2*i4,2);
 cnt=1;
 while abs(1-LL1/LL2)>1e-5
  LL=LL2-eta*d2*(LL2-LL1)/(d2-d1);
 kminusLLxm;
  detandnneg;

%FIFO -- rotate out LL1
  LL1=LL2;
  LL2=LL;
  d1 =d2;
  d2 =determinant;
  cnt=cnt+1;
 end
 Freq(i4,1)=LL2;
 Freq(i4,3)=cnt;
end
Freq(1:numLLs,2)=0.5*sqrt(Freq(1:numLLs,1))/pi;
format short
Freq %FIFO -- rotate out LL1
  LL1=LL2;
  LL2=LL;
  d1 =d2;
  d2 =determinant;
  cnt=cnt+1;
 end
 Freq(i4,1)=LL2;
 Freq(i4,3)=cnt;
end
Freq(1:numLLs,2)=0.5*sqrt(Freq(1:numLLs,1))/pi;
format short
Freq
```

*******************************************
Subroutine Kandm

```
%BUILD STIFFNESS MATRIX
n=round(L/12);
ds=12; % the segment length is one foot
s=[0:ds:n*ds]; % s=0 is at the top of the cable, s=L is at the bottom
s(n)=L;
```

```
%ins=[16 66 106 166 216 266 316;75 8 8 8 8 8 8];
%sumins=(6*8+75);
%W=W-sumins;
%Rho=W/L;Mass=W/386.4;
```

```
Vt=V-Rho*s; % Vt=the vertical component of cable tension at the top of a segment
dldH=L/n/E/A+(asinh(Vt/H)-asinh((Vt-W/n)/H)-(Vt/H)./sqrt((Vt/H).^2+1)+((Vt-
W/n)/H)./sqrt(((Vt-W/n)/H).^2+1))/Rho;
dldV=(1.0./sqrt((Vt/H).^2+1)-1.0./sqrt(((Vt-W/n)/H).^2+1))/Rho;
dhdV=L/n/E/A+((Vt/H)./sqrt((Vt/H).^2+1)-((Vt-W/n)/H)./sqrt(((Vt-W/n)/H).^2+1))/Rho;
deter=dldH.*dhdV-dldV.^2;
temp1=[dhdV./deter;dldV./deter;dldV./deter;dldH./deter];
temp2=reshape(temp1,2,2*(n+1));
temp22=temp2';
kk=temp2(1:2,1:2*(n-1))+temp2(1:2,3:2*n);
kk=kk';
k=zeros(2*(n-1),4);
k(1:2*(n-1),1:2)=kk(1:2*(n-1),1:2);
for i=2:2:2*(n-1);
   k(i,1)=0;
end
k(2*(n-1)-1:2*(n-1),3:4)=k(2*(n-1)-1:2*(n-1),1:2);

k(2*(n-1)-1,1)=0;
k(2*(n-1)-1,2)=0;
k(2*(n-1)  ,2)=0;
k(1:2+2*(n-3),3:4)=temp22(3:4+2*(n-3),1:2);

normalizer=(k(1,1)*k(2,2)-k(1,2)^2)^(0.46);
```

%BUILD MASS MATRIX
```
m=ones(2*(n-1),1);
m=m*Mass/n;
m(1)=m(1)/2;
m(2*(n-1))=m(2*(n-1))/2;
```

```
% add insulator weights at segment boundaries
for i=1,nins,1
  m(ins(1,i))=m(ins(1,i))+ins(2,i)
end
```

*******************************************
Subroutine detandnneg

%CALCULATE DETERMINANT AND # OF NEGATIVE DIAGONAL TERMS
```
nn=2*(n-1);
nneg=0;
determinant=0;

format short e
%row 1 is unchanged
if a(1,1)<0
  nneg=nneg+1;
end
```

```
determinant=a(1,1);

%row 2
a(2,2)=a(2,2)-a(1,2)*a(1,2)/a(1,1);
a(2,3)=a(2,3)-a(1,2)*a(1,3)/a(1,1);
a(2,4)=a(2,4)-a(1,2)*a(1,4)/a(1,1);
if a(2,2)<0
  nneg=nneg+1;
end
determinant=determinant*a(2,2);

%rows 3 to nn-2
for i=3:2:nn-3
  a(i ,1)=a(i,1)-a(i-2,3)^2/a(i-2,1)-a(i-1,3)^2/a(i-1,2);
  a(i ,2)=a(i,2)-a(i-2,3)*a(i-2,4)/a(i-2,1)-a(i-1,3)*a(i-1,4)/a(i-1,2);
  if a(i,1)<0
    nneg=nneg+1;
  end a(i+1,2)=a(i+1,2)-a(i-2,4)^2/a(i-2,1)-a(i-1,4)^2/a(i-1,2)-a(i,2)^2/a(i,1);
  a(i+1,3)=a(i+1,3)-a(i,2)*a(i,3)/a(i,1);
  a(i+1,4)=a(i+1,4)-a(i,2)*a(i,4)/a(i,1);
    if a(i+1,2)<0
    nneg=nneg+1;
  end
  determinant=determinant*a(i,1)*a(i+1,2);
end %row nn-1
a(nn-1,3)=a(nn-1,3)-a(nn-3,3)^2/a(nn-3,1)-a(nn-2,3)^2/a(nn-2,2);
a(nn-1,4)=a(nn-1,4)-a(nn-3,3)*a(nn-3,4)/a(nn-3,1)-a(nn-2,3)*a(nn-2,4)/a(nn-2,2);
if a(nn-1,3)<0
  nneg=nneg+1;
end
determinant=determinant*a(nn-1,3);

%row n
a(nn,4)=a(nn,4)-a(nn-3,4)^2/a(nn-3,1)-a(nn-2,4)^2/a(nn-2,2)-a(nn-1,4)^2/a(nn-1,3);
if a(nn,4)<0
  nneg=nneg+1;
end
determinant=determinant*a(nn,4);
```

******************************************
Subroutine kminusLLxm

```
a=k;
for i=1:2:2*(n-1)-3
  a(i ,1)=a(i ,1)-LL*m(i);
  a(i+1,2)=a(i+1,2)-LL*m(i+1);
end
a(2*(n-1)-1,3)=a(2*(n-1)-1,3)-LL*m(2*(n-1)-1);
a(2*(n-1) ,4)=a(2*(n-1) ,4)-LL*m(2*(n-1));
a=a/normalizer;
```

We claim:

1. The method of determining the tension in a flexible member which comprises calculating the natural frequency of the member when subjected to its design tension; calculating the natural frequency of the member at increments above and below its design tension; determining the actual natural frequency in said member; and comparing the measured natural frequency with the calculated natural frequencies.

2. The method of claim 1 further including calculating a series of natural frequencies at the design tension and at each increment above and below the design tension in said member.

3. The method of claim 2 further including determining a series of actual natural frequencies in said member.

4. The method of claim 1 further including using the wind to excite the member.

5. The method of claim 3 further including comparing the series of actual natural frequencies with the series of calculated natural frequencies.

* * * * *